United States Patent [19]
Lee

[11] Patent Number: 5,226,428
[45] Date of Patent: Jul. 13, 1993

[54] TONGUE AND LINGUAL FRENUM MEASURING DEVICES

[76] Inventor: Seoung-Ho Lee, 220 Dogwood, Plano, Tex. 75075

[21] Appl. No.: 923,624

[22] Filed: Aug. 3, 1992

[51] Int. Cl.$^5$ .............................................. A61B 5/03
[52] U.S. Cl. ....................................... 128/777; 33/514
[58] Field of Search ............................... 128/777, 630; 33/511–514, 483, 494

[56] References Cited
U.S. PATENT DOCUMENTS

D. 276,032  4/1883  Hamilton ............................ 33/494
443,652  12/1890  Jewell et al. ........................... 33/483
4,641,436  2/1987  Tzen et al. ............................ 33/483

Primary Examiner—Lee S. Cohen
Assistant Examiner—Brian L. Casler

[57] ABSTRACT

A set of different rulers for the measurements of the abnormal tongue and its frenum size. We can get useful information about the various border movements of the tongue from the evaluation of the measurement results with this device. These rulers will help to improve various treatment procedures and evolve diagnostic methodologies in every related field of the specialties as well as provide relatively more precise guide-lines.

4 Claims, 9 Drawing Sheets

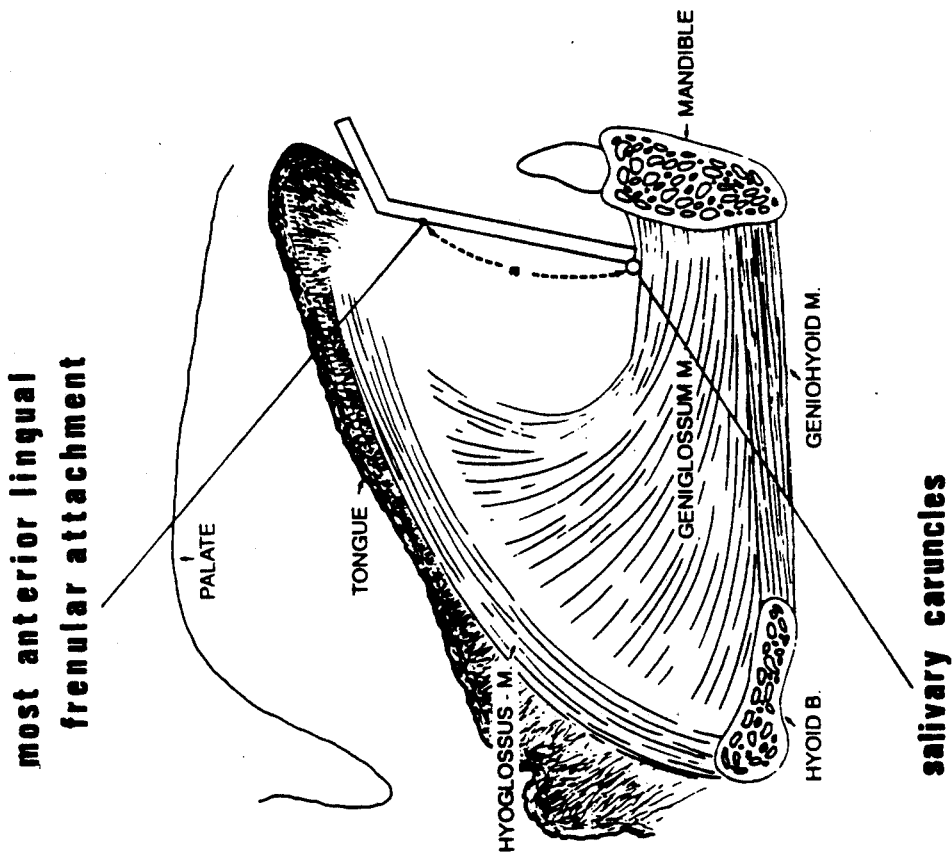

TONGUE AND LINGUAL FRENUM MEASURING DEVICES

BRIEF SUMMARY

This invention relates to oral measuring devices, and more particularly to devices adapted to measure the tongue and the lingual frenum.

This invention comprises a five-piece set of tongue rulers made of translucent plastic and calibrated in millimeters along the median portion thereof: a main ruler and four accessory rulers.

The main ruler is used for linear measurements of the tongue, the superior border of the lingual frenum and the median length of the lingual frenum.

accessory rulers I, II, III and IV are to be used to take the linear measurements of the inferior and anterior borders on the lingual frenum.

For each measurement, the ruler being used should be adjusted to the median line of the dental arch by using the green stripes on each ruler as a guide. The slotted portion of the ruler fits on the lingual frenum, and the strait aids in stabilizing the instrument for accuracy in measuring. The length of the patient's frenum determines which of the accessory rulers is used.

The main object of this invention is to provide convenience and uniformity in the accurate evaluation of the limitations of tongue movements and its frenular size.

Therefore, this invention has been designed to conform to standard conventions of manufacturing and to be simply constructed and easy to use.

This device will be affordable, durable, and practical for application by specialists in various medical fields including, but not limited to: oral and plastic surgery, general and every specialized dentistry and speech pathology. Its application relates to problems including, but not limited to: speech, dentition, oral musculature, mucogingival structures and orthodontic post-op.

Further objects and advantages of my invention will become apparent from a consideration of the drawings and ensuing description of it.

BRIEF DESCRIPTION OF THE DRAWINGS

FIG. 9 shows a longitudinal cross section of the tongue with the proper positioning of the accessory rulers for the measurement of the anterior border of the lingual frenum.

DETAILED DESCRIPTION

Figure 1:
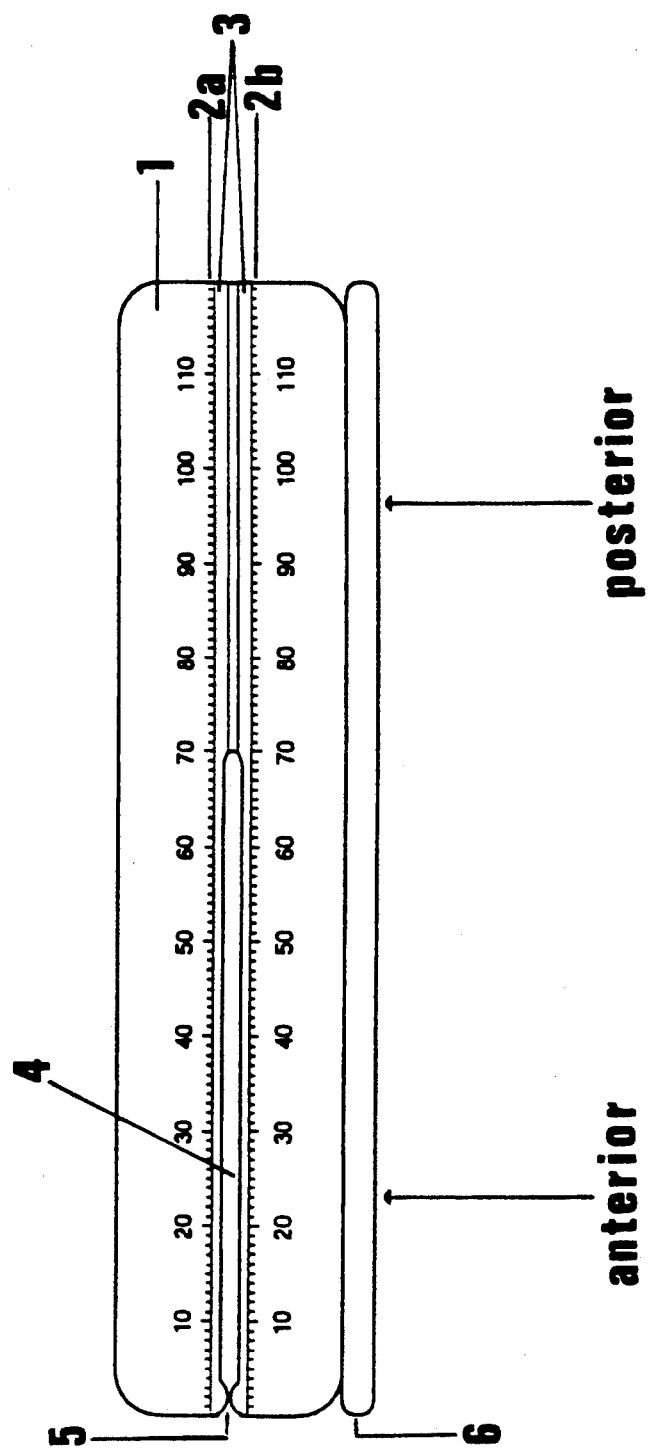
FIG. 1 shows both a top view of the main ruler and its thickness.

FIGS. 1-5 illustrate the five different rulers which make up the tongue measuring device. The device comprises a main ruler (FIG. 1) and four accessory rulers (FIGS. 2-5). The body of each ruler (1) is made of translucent plastic material, has scale indicia calibrated in millimeters (2a and 2b), is slotted (4) at the anterior end where a strait (5) characterizes the opening of the slot. The median portion of each ruler is colored green (3) along each scale indicium, providing a contrasting background upon which the measurements can easily be read against the pink color of the oral cavity.

The main ruler (FIG. 1) is a flat plane. The accessory rulers (FIGS. 2-5) are bent at the 10 mm, 20 mm, 30 mm, and 40 mm marks (respectively) from the anterior end of the rulers. The angle of the bend is variable between 90 and 180 degrees.

FIGS. 2-5: Features 1, 2a, 2b, 3, 4 and 5 are described above for FIG. 1.

The sequencing of the numerals on the scale indicia (2a, 2b) for the accessory rulers (FIGS. 2-5) is reversed on either side of the median line.

FIG. 1 shows a top view of the main ruler (1) and a side view (6) representing its thickness, which is variable and dependent on the material of the ruler body. The anterior end of the ruler is positioned in the mouth and is fitted onto the lingual frenum via the slotted space (4). The strait (5) of the slot secures the ruler during the measurement.

Figure 2:
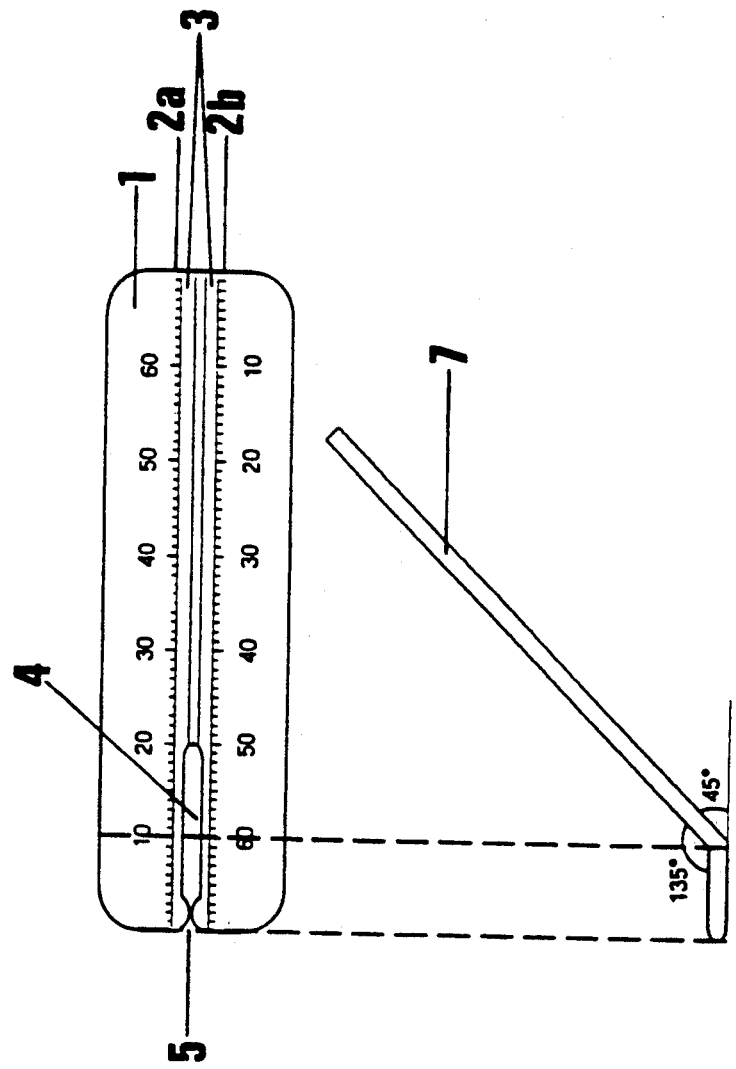
FIG. 2 shows top and lateral views of accessory ruler I.

FIG. 2 shows a top view of the accessary ruler I and a side view representing its thickness and bend(7).

Figure 3:
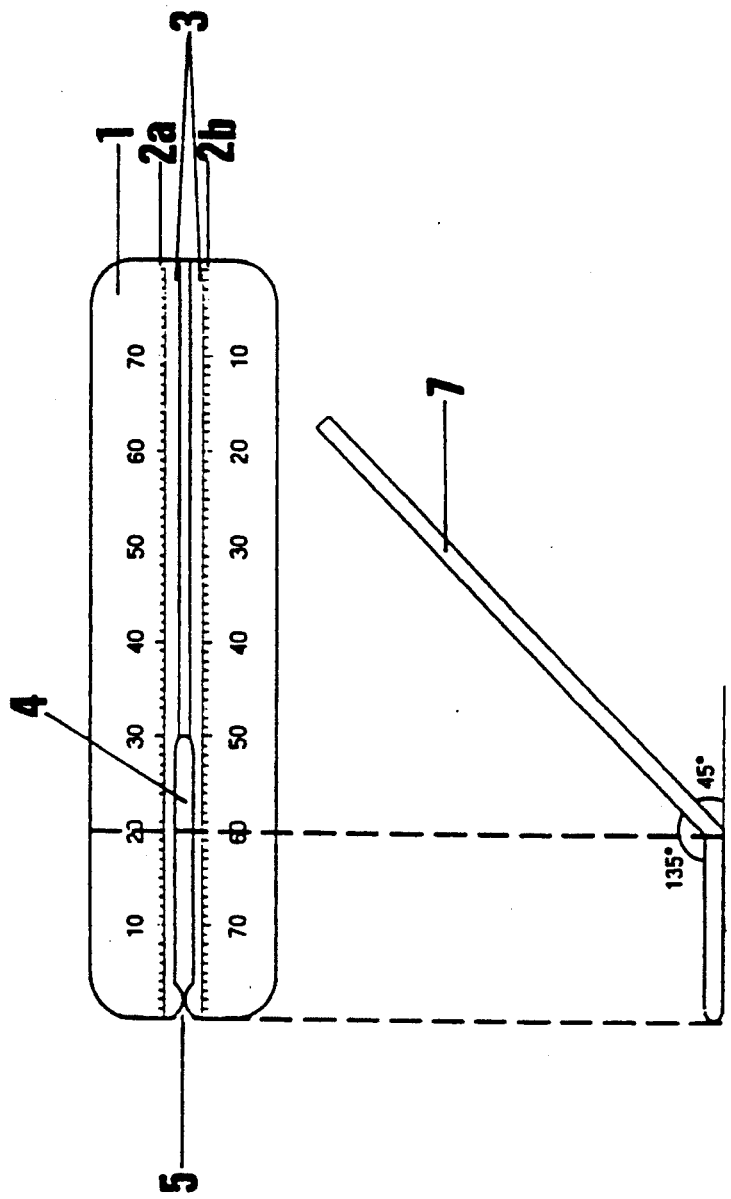
FIG. 3 shows top and lateral views of accessory ruler II.

FIG. 3 shows a top view of the accessary ruler II and a side view representing it s thickness and bend(7).

Figure 4:
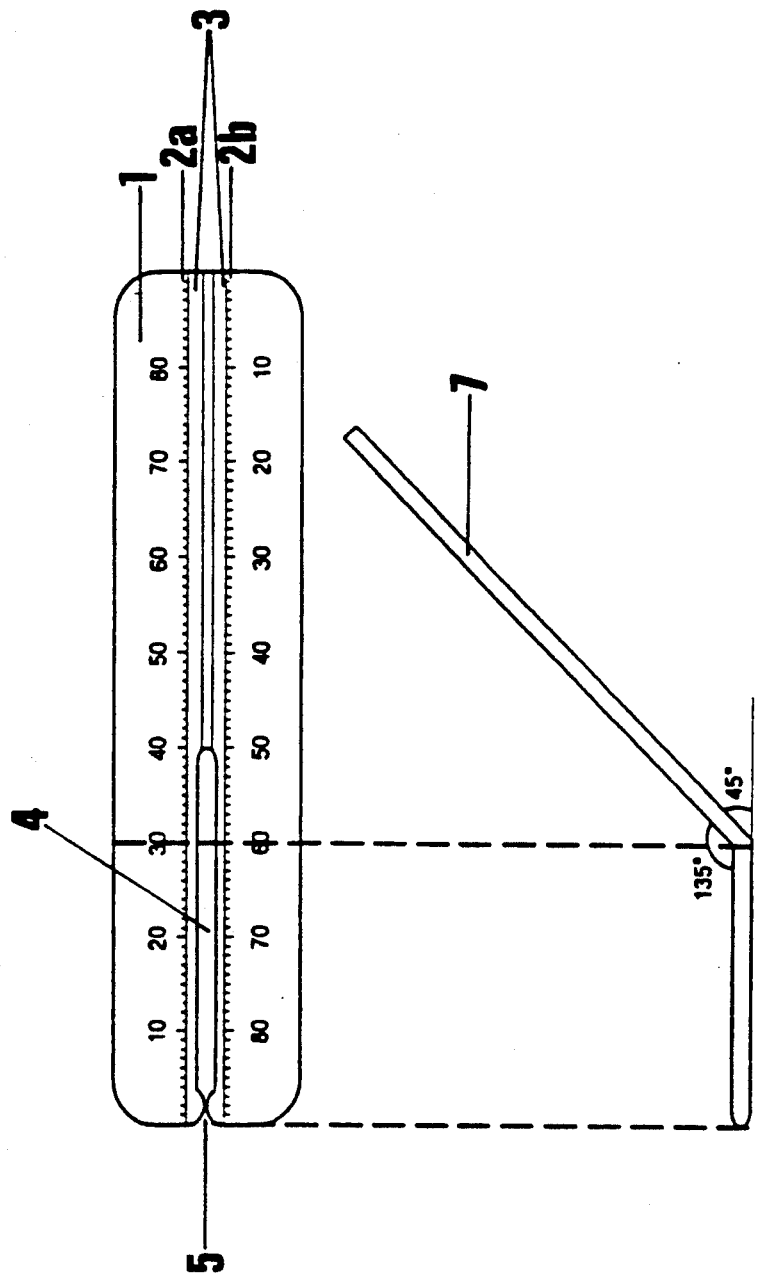
FIG. 4 shows top and lateral views of accessory ruler III.

FIG. 4 shows a top view of the accessary ruler III and a side view representing its thickness and bend(7).

Figure 5:
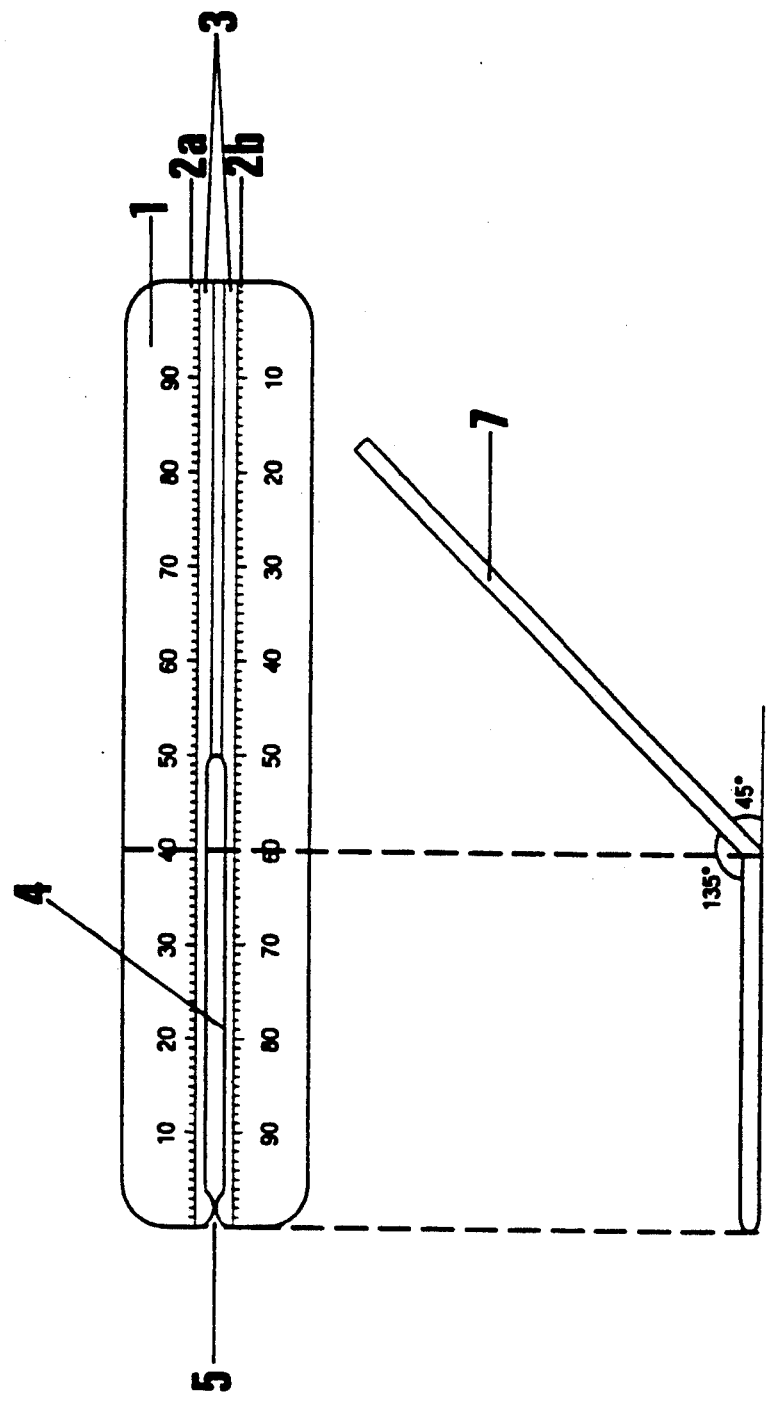
FIG. 5 shows top and lateral views of accessory ruler IV.

FIG. 5 shows a top view of the accessary ruler IV and a side view representing its thickness and bend(7).

Figure 6:
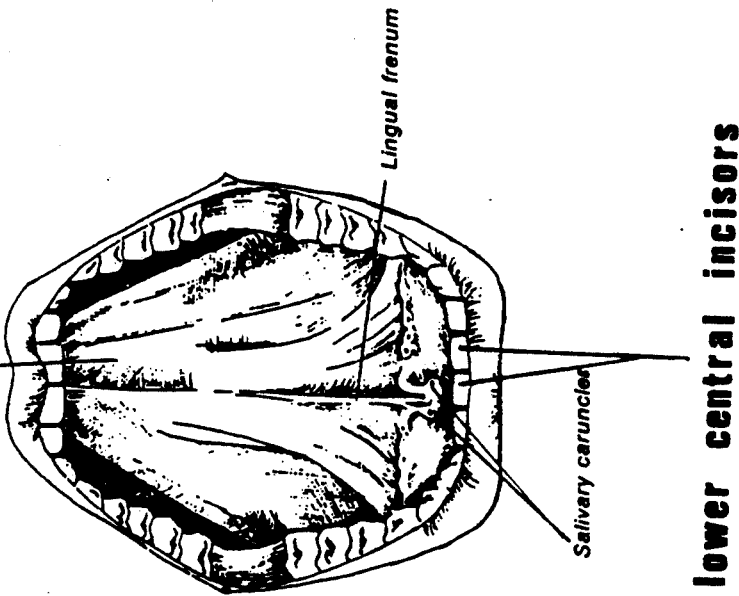
FIG. 6 shows a front view of the oral cavity showing the anatomical positions of the ventral surface of the tongue, the lingual frenum, the salivary caruncles and the lower(mandibular) central incisors.

FIG. 6 shows the oral cavity of the mouth and establishes the anatomical relationships among the ventral surface of the tongue, the lingual frenum, the salivary caruncles and the lower(mandibular) central incisors.

Figure 7:
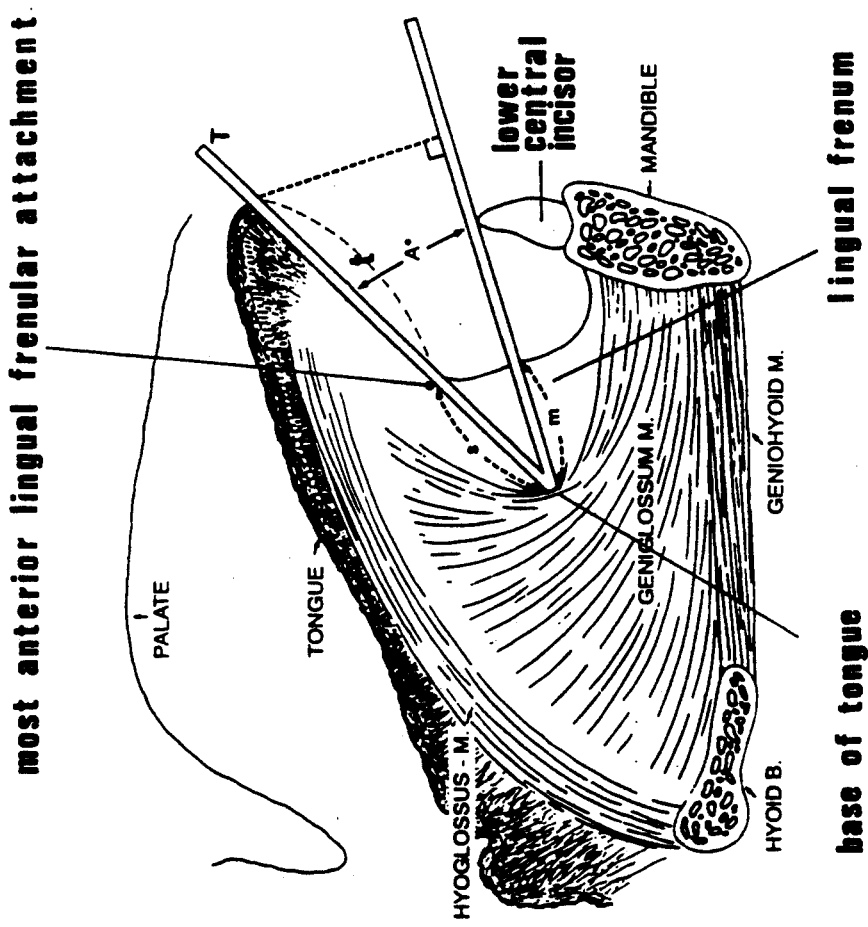
FIG. 7 shows a longitudinal cross sectional view of the tongue and the placement of the main ruler in two different positions for measuring the superior marginal length, linear measurements of the ventral surfaces and the median length of the lingual frenum.

FIG. 7 illustrates the method of measurement using the main ruler. For these measurements the tongue must be in the maximum voluntary anteriorly protruding tongue position. The ruler is positioned as described above (FIG. 1). Four measurements are shown: (t) is the maximum ventral length of the tongue; (t) is the linear measurement of the tongue tip from the lingual frenular attachment to the tongue tip when the tongue is at the maximum anteriorly protruding position voluntarily: (s) is the length of the superior border of the lingual frenum from the base of the tongue to the frenular attachment of the ventral surface of the tongue at the maximum anteriorly voluntary protruded tongue; (m) is the median length of the lingual frenum during the maximum mouth opening voluntarily. When measuring (m), the posterior portion of the ruler should touch the tip of the lower central incisors.

Figure 8:
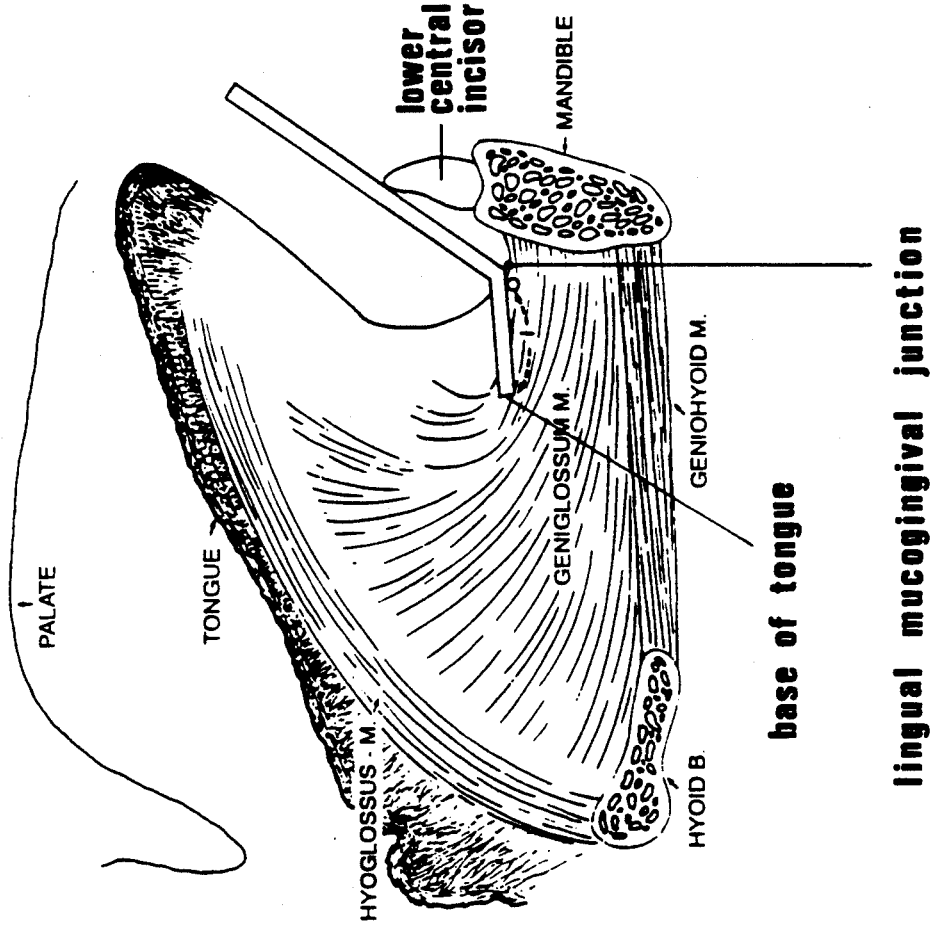
FIG. 8 shows a longitudinal cross section of the tongue with the proper positioning of the accessory rulers used to measure the inferior border of the lingual frenum.

FIG. 8 illustrates the method of measurement using one of the accessory rulers. (i) is the length of the inferior border of the lingual frenum from the base of the tongue to the mucogingival junction of the lingual aspect of the lower anteriors when the tongue is at the maximum elevated position during maximum mouth opening. At the same time, the posterior portion of the ruler should touch the tip of the lower central teeth.

FIG. 9 illustrates the method of measurement using one of the accessary rulers to measure the anterior border of the lingual frenum (a) from the sublingual gland opening to the lingual frenular attachment of the ventral surface of the tongue during the maximum voluntary mouth opening.

As various possible embodiments might be made of the above invention without departing form the scope of the invention, it is to be understood that all matter herein described or shown in the accompanying drawings is to be interpreted as illustrative rather than as limiting. Thus, the drawings will be appreciated as exemplary of a preferred embodiment of the invention.

What is claimed is:

1. A tongue measuring kit comprising a set of five rulers each of which includes two horizontal scales, an upper longitudinal edge, a lower longitudinal edge, an anterior and posterior end, and a median portion therebetween, one of said scales being positioned between the median portion and the upper longitudinal edge of said ruler and the other said scale being positioned between the median portion and the lower longitudinal edge of said ruler;

a horizontal slot means for fitting each ruler to the lingual frenum, said slot means being positioned in the median portion of the ruler, parallel to and between said horizontal scales and is open from the anterior end of said ruler forming a means for providing stability when applying the ruler to take measurements, said means comprising a strait at the median portion of the anterior end.

2. The kit according to claim 1, wherein said set of five rulers further comprises a main ruler and four accessory rulers, wherein the main ruler is flat and each accessory ruler comprises a configuration wherein a bent anterior end forms an angle with the posterior end and said bent anterior end varies in length and is substantially shorter than the posterior end, said angle is between 90 and 180 degrees.

3. The kit according to claim 2, wherein the two horizontal scales of each accessory ruler comprise numerals and the sequencing of the numerals of said scales is reversed on either side of the median portion of said accessory rulers.

4. The kit according to claim 1 wherein, the two horizontal scales are metric.

* * * * *